Aug. 21, 1973 P. ECKE, JR Plant Pat. 3,392
POINSETTIA PLANT
Filed March 30, 1972
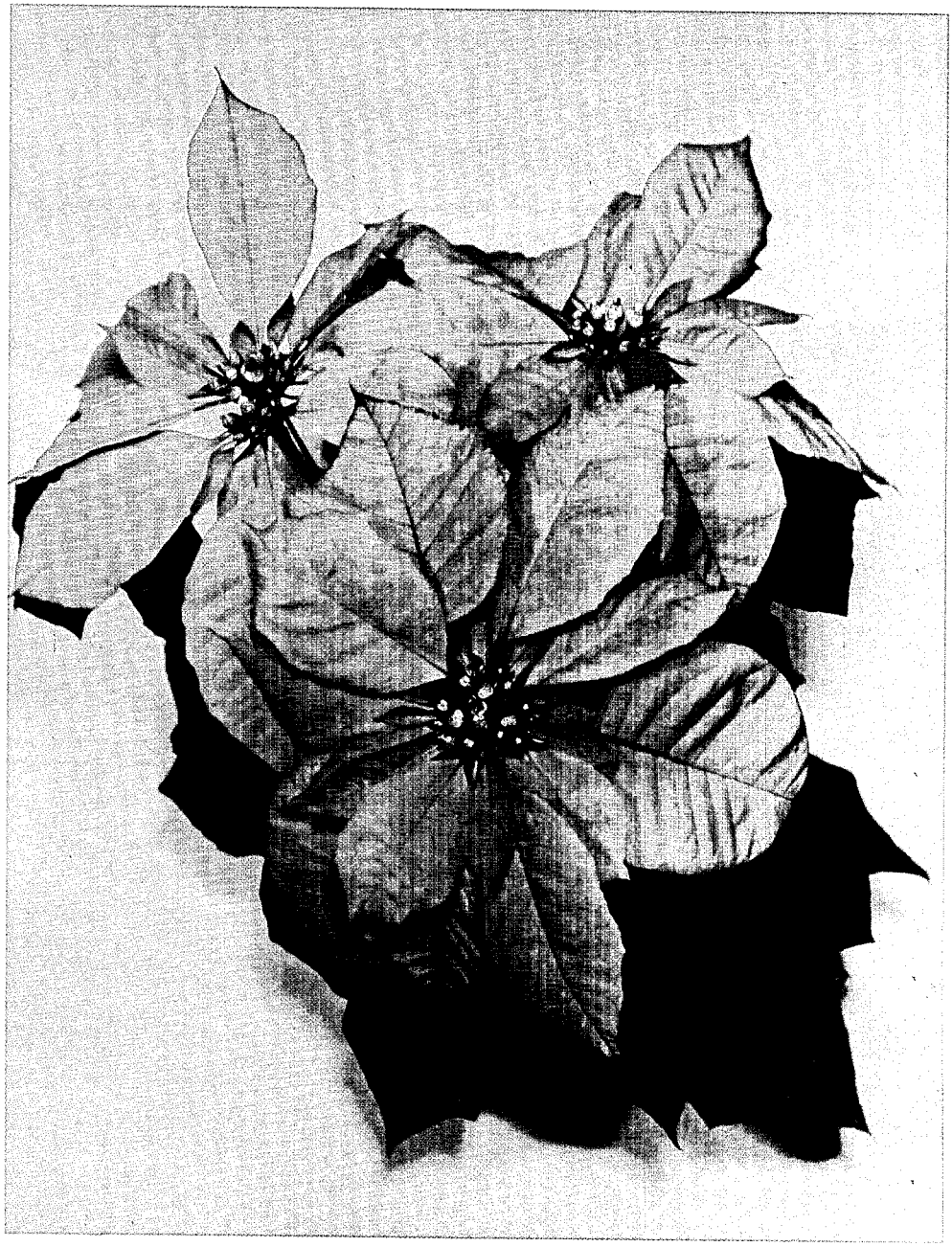

United States Patent Office

Plant Pat. 3,392
Patented Aug. 21, 1973

3,392

POINSETTIA PLANT

Paul Ecke, Jr., Encinitas, Calif., assignor to Paul Ranch Ecke, Encinitas, Calif.

Filed Mar. 30, 1972, Ser. No. 239,831
Int. Cl. A01h *5/00*
U.S. Cl. Plt.—86 1 Claim

The present invention relates to a new and distinct variety of poinsettia plant, botanically known as *Euphorbia pulcherrima,* which was discovered by me as a cultivated sport of the poinsettia variety known as "Annette Hegg" (Plant Pat. No. 2,962), said discovery having been made by me in one of my greenhouses located at Encinitas, Calif.

At the time of my discovery aforesaid, I was growing in my greenhouses at Encinitas various poinsettia varieties, including many plants of the patented variety "Annette Hegg." In the course of these growing operations, my attention was attracted to one particular plant among those of "Annette Hegg" which bore bracts of a substantially brighter red color than the normal red bracts of "Annette Hegg." Close inspection of this particular plant showed that it had sported, so I carefully preserved the sport and kept it under close observation. In due course, I asexually reproduced the sport by vegetative cuttings taken therefrom and planted in my greenhouses at Encinitas. Continued observations and tests of the original sport and its progeny derived from the vegetative cuttings aforesaid, fully confirmed that the brilliant red bracts come true and remain stable, and that their brighter red color is even more evident and pronounced when viewed under fluorescent light, contrary to the normal bract color of "Annette Hegg."

Except for its brighter red bract color, which is more brilliant than that of all other red sports of "Annette Hegg" of which I am aware, my new sport is substantially identical with its parent variety "Annette Hegg," and thus constitutes a new and commercially valuable variety which is distinguished from all other poinsettia varieties, as evidenced by the following unique combination of principal features which are outstanding therein:

(1) A short-growing and compact plant habit;

(2) A uniform and fast rooting habit;

(3) A self-branching habit resulting in multiple blooms without pinching off the terminal buds as required for other poinsettia varieties;

(4) Attractive green foliage of lighter color than the foliage of such varieties as "Paul Mikkelsen" (Plant Pat. No. 2,328);

(5) A distinctive, attractive and more brilliant red bract color than the bracts of the variety, "Annette Hegg," (Plant Pat. No. 2,962); and (6) Long-lasting plant qualities.

The accompanying drawing shows a typical specimen plant of my new poinsettia variety as depicted in color as nearly true as it is reasonably possible to make the same in a color illustration of this character.

Although the details of my new sport, except for its brighter red bract color, are generally similar to those described in Plant Pat. No. 2,962, to which reference may be readily had, the following brief description of the new sport is given for convenience, with color terminology in accordance with Wilson's Horticultural Colour Chart, except where general color terms of ordinary dictionary significance are obvious:

Parentage: Sport of "Annette Hegg."

Propagation: Holds its distinguishing characteristics through succeeding propagations by vegetative cuttings.

Locality where grown and observed: Encinitas, Calif.

Form: Short-growing; compact.

Habit of growth: Self-branching; does not require pinching off terminal buds to produce multiple blooms.

Rooting habit: Very uniform; very fast.

Blooming habit: More predictable than other varieties, and is normally considered as a "9-week" variety.

Blooming season: Blooms predictably in time for Christmas season and well beyond through at least the month of April; is also a good variety for flowering in spring, summer and autumn.

Foliage:

*Shape.*—Normal; most typical leaves are more ovate-acuminate and only seldom lobed.

*Color.*—New foliage—upper side—Pod Green, Plate 061, under side—Pod Green, Plate 061/1. Old foliage—upper side—Spinach Green, Plate 0960; under side—Spinach Green, Plate 0960/2.

Bracts:

*Shape.*—Obovate; relatively broad.

*Color.*—Near Blood Red, Plate 820/2; more brilliant than bract color of "Annette Hegg"; brightness of red color is even more intensified when viewed under fluorescent light.

Flowers (Cyathia): Form earlier and are more numerous and stronger than those of "Paul Mikkelsen"; have a strong yellow pollen; very slight tendency to split; do not drop off prematurely and last as long as the bracts.

Reproductive organs:

*Stamens.*—Quite numerous; from about ⅛ inch to ¼ inch long. Color—Currant Red, Plate 821/2.

*Pollen.*—Color—Canary Yellow, Plate 2.

*Styles.*—Color—Blood Red, Plate 820.

*Ovaries.*—Color—Scheele's Green, Plate 860/1.

*Nectar cups.*—Color—Lemon Yellow, Plate 4/1.

General observations: The new variety generally resembles the variety "Annette Hegg" in all respects except for the bract color which is more brilliant than the normal red bract color of "Annette Hegg," and the brilliance becomes even more intensified when viewed under fluorescent light.

I claim:

1. A new and distinctive variety of poinsettia plant, substantially as herein shown and described, characterized particularly as to novelty by the unique combination of a short-growing and compact plant habit, a uniform and fast rooting habit, a self-branching habit resulting in multiple blooms without pinching off the terminal buds as required for other poinsettia varieties, attractive green foliage of lighter color than the foliage of such varieties as "Paul Mikkelsen" (Plant Pat. No. 2,328), a distinctive, attractive and more brilliant red bract color than the bracts of the variety "Annette Hegg" (Plant Pat. No. 2,962), and long-lasting plant qualities.

No references cited.

ROBERT E. BAGWILL, Primary Examiner